United States Patent [19]
Treybig et al.

[11] Patent Number: 4,957,640

[45] Date of Patent: Sep. 18, 1990

[54] CORROSION PREVENTION WITH COMPOSITIONS PREPARED FROM ORGANIC FATTY AMINES AND NITROGEN-CONTAINING AROMATIC HETEROCYCLIC COMPOUNDS

[75] Inventors: Duane S. Treybig; Robert G. Martinez, both of Lake Jackson, Tex.

[73] Assignee: The Dow Chemical Company, Midland, Mich.

[21] Appl. No.: 318,772

[22] Filed: Mar. 3, 1989

Related U.S. Application Data

[60] Continuation-in-part of Ser. No. 168,296, Mar. 15, 1988, abandoned, which is a division of Ser. No. 787,819, Oct. 15, 1985, Pat. No. 4,761,473.

[51] Int. Cl.$^5$ .................... E21B 41/02; C23F 11/00
[52] U.S. Cl. ................... 252/8.555; 252/392; 422/16; 422/7
[58] Field of Search ............... 252/8.555, 392

[56] References Cited

U.S. PATENT DOCUMENTS

| | | | |
|---|---|---|---|
| 2,705,714 | 4/1955 | Webb et al. | 544/406 |
| 4,100,099 | 7/1978 | Lee et al. | 252/403 X |
| 4,102,804 | 7/1978 | Clouse et al. | 252/392 X |
| 4,106,904 | 8/1978 | Oudealink et al. | 252/8.555 X |
| 4,174,370 | 11/1979 | Oudealink et al. | 252/8.555 X |
| 4,390,437 | 6/1983 | Lee et al. | 252/403 X |
| 4,402,907 | 9/1983 | Clark | 252/392 X |
| 4,446,056 | 5/1984 | Thompson | 252/8.555 X |
| 4,515,708 | 5/1985 | Haslegrave et al. | 252/390 |
| 4,522,785 | 6/1985 | D'Errico | 252/392 X |
| 4,631,138 | 12/1986 | Johns et al. | 252/8.555 |

*Primary Examiner*—Matthew A. Thexton
*Assistant Examiner*—Chhaya Sayala

[57] ABSTRACT

Corrrosion inhibiting compositions containing compositions prepared from (1) nitrogen-containing aromatic heterocyclic compound having at least one group of either (a) a carboxylic acid, (b) carboxylic acid ester, (c) carboxylic acid annhydride, (d) carboxylic acid halide, (e) or combination thereof, such as 2-pyridinecarboxylic acid, and (2) an organic fatty amine such as a mixture of $C_{10}$ to $C_{21}$ fatty amines.

9 Claims, No Drawings

CORROSION PREVENTION WITH COMPOSITIONS PREPARED FROM ORGANIC FATTY AMINES AND NITROGEN-CONTAINING AROMATIC HETEROCYCLIC COMPOUNDS

CROSS-REFERENCE TO RELATED APPLICATIONS

This is a continuation-in-part of application Ser. No. 168,296 filed Mar. 15, 1988 now abandoned which is a division of application Ser. No. 787,819 filed Oct. 15, 1985 (now U.S. Pat. No. 4,761,473 issued Aug. 2, 1988). All of the above prior applications are incorporated herein by reference in their entirety.

FIELD OF THE INVENTION

The present invention pertains to novel compositions prepared by reacting nitrogen-containing aromatic heterocyclic compounds substituted with at least one group of a carboxylic acid, carboxylic acid ester, carboxylic acid anhydride, carboxylic acid halide or combination thereof, and organic fatty amines.

BACKGROUND OF THE INVENTION

During the drilling and servicing of oil and gas wells, the metal tools and equipment associated therewith are susceptible to corrosion. It is therefore highly desirable to have corrosion inhibitors for the protection of these metal tools and equipment. The present invention provides corrosion inhibitors for use at both low and high temperatures. The deeper the wells, the higher the temperature; therefore there is a need for inhibitors suitable for use at both low and high temperatures.

SUMMARY OF THE INVENTION

One aspect of the present invention concerns new compositions of matter which comprises the reaction product of
  (1) at least one aromatic heterocyclic material, except pyrazine, having one or more rings, at least one nitrogen atom and containing at least one group selected from
    (a) carboxylic acid,
    (b) carboxylic acid ester,
    (c) acyclic carboxylic acid anhydride,
    (d) carboxylic acid halide or
    (e) combination thereof with
  (2) an organic amine represented by the formulas $$H_2N{+CH_2\}_{\overline{p}}CH_3,$$

$$H_2N{+CH_2\}_{\overline{p}}{+CH=CH\}_{\overline{n}}CH_3,$$

$$H_2N{+\!\!+\!CH_2\}_{\overline{m}}{-}NH\}_{\overline{m}}{-}(CH_2\}_{\overline{m}}{-}NH_2,$$

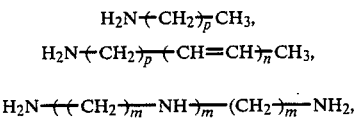

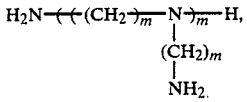

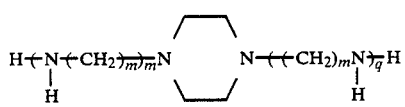

$$H_2N{+CH_2\}_{\overline{m}}{-}NH{+CH_2\}_{\overline{p}}CH_3, \text{ or}$$

$$H_2N{+CH_2\}_{\overline{m}}{-}NH(CH_2\}_{\overline{p}}{+CH=CH\}_{\overline{n}}CH_3, \text{ or}$$

wherein m has a value from 1 to about 10, n has a value from 1 to about 5, p has a value from 7 to about 72, q has a value from zero to about 10; and wherein the carbon-carbon double bond (—CH=CH)— is located anywhere through the saturated hydrocarbon chain ((—CH$_2$);

(3) optionally reacted or neutralized with a mineral acid or an organic acid having from about 1 to about 36 carbon atoms, preferably from about 1 to about 24 carbon atoms, most preferably an alkyl group having from about 1 to about 6 carbon atoms; and
wherein components (1) and (2) are present in —CO— groups to —NH$_2$ and/or —NH— groups of from about 0.1:1 to about 1.2:1, preferably from about 0.75:1 to about 1.2:1, most preferably from about 0.9:1 to about 1.1:1 and component (3) is present in a quantity which provides a ratio of mineral acid or carboxylic acid to reactive amine hydrogen of the product formed from the reaction of components (1) and (2) of from about zero:1 to about 2:1, preferably from about 0.75:1 to about 1.5:1, most preferably from about 0.9:1 to about 1.1:1.

Another aspect of the present invention concerns new compositions of matter which comprise the reaction product of
  (1) at least one pyrazine compound containing at least one group selected from
    (a) carboxylic acid,
    (b) carboxylic acid ester,
    (c) acyclic carboxylic acid anhydride,
    (d) carboxylic acid halide or
    (e) combination thereof with
  (2) an organic amine represented by the formulas $$H_2N{+\!\!+\!CH_2\}_{\overline{m}}{-}NH\}_{\overline{m}}{-}(CH_2\}_{\overline{m}}{-}NH_2,$$

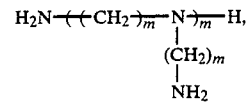

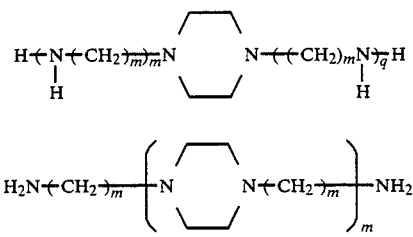

$$H_2N{+CH_2\}_{\overline{m}}{-}NH{+CH_2\}_{\overline{p}}CH_3, \text{ or}$$

$$H_2N{+CH_2\}_{\overline{m}}{-}NH(CH_2\}_{\overline{p}}{+CH=CH\}_{\overline{n}}CH_3, \text{ or}$$

wherein m has a value from 1 to about 10, n has a value from 1 to about 5, p has a value from 7 to about 72, q has a value from zero to about 10; and wherein the carbon-carbon double bond (—CH=CH)— is located anywhere through the saturated hydrocarbon chain ((—CH$_2$)$_p$); and (3) optionally reacted or neutralized with a mineral acid or an organic acid having from about 1 to about 36 carbon atoms, preferably from about 1 to about 24 carbon atoms, most preferably an alkyl group having from about 1 to about 6 carbon atoms; and wherein components (1) and (2) are present in quantities which provide a ratio of —CO— groups to —NH$_2$ and/or —NH— groups of from about 0.1:1 to about 1.2:1, preferably from about 0.75:1 to about 1.2:1, most preferably from about 0.9:1 to about 1.1:1 and component (3) is present in a quantity which provides a ratio of mineral acid or carboxylic acid to reactive amine hydrogen of the product formed from the reaction of components (1) and (2) of from about zero:1 to about 1, preferably from about 0.75:1 to about 1.5:1, most preferably from about 0.9:1 to about 1.1:1.

Another aspect of the present invention pertains to a method for preventing or reducing the corrosion of a metal composition in contact with down hole well fluids, which method comprises contacting the surface of said metal composition with an effective amount of a composition which comprises the reaction product of (1) at least one aromatic heterocyclic compound having one or more rings, at least one nitrogen atom and containing at least one group selected from
  (a) carboxylic acid,
  (b) carboxylic acid ester,
  (c) acyclic carboxylic acid anhydride,
  (d) carboxylic acid halide or
  (e) combination thereof with
(2) an organic amine having from about 1 to about 72 carbon atoms, preferably from about 10 to about 24 carbon atoms; and
(3) optionally reacted or neutralized with a mineral acid or an organic acid having from about 1 to about 36 carbon atoms, preferably from about 1 to about 24 carbon atoms, most preferably an alkyl group having from 1 to about 6 carbon atoms; and wherein components (1) and (2) are present in quantities which provide a ratio of —CO— groups to —NH$_2$ and/or —NH— groups of from about 0.1:1 to about 1.2:1, preferably from about 0.75:1 to about 1.2:1, most preferably from about 0.9:1 to about 1.1:1 and component (3) is present in a quantity which provides a ratio of mineral acid or carboxylic acid to reactive amine hydrogen of the product formed from the reaction of components (1) and(2) of from about zero:1 to about 2:1, preferably from about 0.75:1 to about 1.5:1, most preferably from about 0.9:1 to about 1.1:1.

DETAILED DESCRIPTION OF THE INVENTION

The corrosion inhibitors of the present invention are prepared by reacting at least one nitrogen containing aromatic heterocyclic compound having at least one group of either a carboxylic acid, carboxylic acid ester, carboxylic acid anhydride, carboxylic acid halide or their combination with an organic amine or mixture of such compounds at a temperature of from about 0° C. to about 300° C. The preferred temperature for the reaction of a nitrogen containing aromatic heterocyclic compound having at least one group of carboxylic acid anhydride, carboxylic acid halide or their combination with an amine is from about 0° C. to about 150° C., most preferably from about 0° C. to about 100° C. The preferred temperature for the reaction of a nitrogen containing aromatic heterocyclic compound having at least one group of carboxylic acid, carboxylic acid ester, or their combination with an amine is from about 150° C. to 250° C., most preferably from about 180° C. to 230° C. These reactions are carried out for a time period that is sufficient to complete the reaction. This time period is usually from about 10 minutes (600 s) to about 48 hours (172,800 s), preferably from about 30 minutes (1800 s) to about 12 hours (43,200 s), most preferably from about 30 minutes (1800 s) to about 2 hours (7200 s). These reactions can be carried out neat or in the presence of solvent. These reactions are usually conducted either under reduced pressure, atmospheric pressure or superatmospheric pressure in an inert atmosphere such as, for example, nitrogen, helium, neon, xenon, argon, mixtures thereof and the like.

Suitable nitrogen containing compounds which can be employed herein include, for example, pyrazines, pyrimidines, pyridazines, quinolines, isoquinolines, cinnolines, or pyridines. These nitrogen containing compounds can, if desired, contain saturated aliphatic hydrocarbon, unsaturated aliphatic hydrocarbon or aromatic hydrocarbon substitutents or any combination thereof. Likewise, these nitrogen containing compounds can, if desired, be free of any such substituents. Particularly, they can be free of unsaturated hydrocarbon substitutents.

Particularly suitable nitrogen containing aromatic heterocyclic compounds having at least one carboxylic acid group which can be employed herein include, for example, 2-pyrazinecarboxylic acid; 2,3-pyrazinedicarboxylic acid; 2,5-pyrazinedicarboxylic acid; 2,6-pyrazinedicarboxylic acid; 2,3,5,6-pyrazinetetracarboxylic acid; 5-methyl-2-pyrazinecarboxylic acid; 6-methyl-2-pyrazinecarboxylic acid; 5,6-dimethyl-2-pyrazinecarboxylic acid; 2-pyridinecarboxylic acid; 3-pyridinecarboxylic acid; 2,3-pyridinedicarboxylic acid; 2,6-pyridinedicarboxylic acid; 3,5-pyridinedicarboxylic acid; 5-butyl-2-pyridinecarboxylic acid; 3,5-dimethyl-2-pyridinecarboxylic acid; 6-chloro-2-pyridinecarboxylic acid; 3-mercapto-2-pyridinecarboxylic acid; 2,2'-dithiobis-3-pyridinecarboxylic acid; 6,6'-dithiobis-3-pyridinecarboxylic acid; 2-pyridineacetic acid; 3-pyridineacetic acid hydrochloride; 4-pyrimidinecarboxylic acid; 4,6-pyrimidinedicarboxylic acid; 3-pyridazinecarboxylic acid; 2-quinoxalinecarboxylic acid; 2-quinolinecarboxylic acid; 4-hydroxy-2-quinolinecarboxylic acid; 4,8-dihydroxy-2quinolinecarboxylic acid; 1-isoquinolinecarboxylic acid; 4-cinnolinecarboxylic acid; 4-hydroxy-7-methyl-1,8-naphthyridine-3-carboxylic acid; 2-phenyl-4-quinolinecarboxylic acid; mixtures thereof and the like.

Particularly suitable nitrogen containing aromatic heterocyclic compounds having at least one carboxylic acid ester group which can be employed herein include, for example, pyrazinecarboxylic acid methyl ester; pyrazinecarboxylic acid ethyl ester; 4-pyridinecarbxylic acid methyl ester; 4-methyl-3-pyridinecarboxylic acid methyl ester; 2-pyridinecarboxylic acid ethyl ester (2-ethylpicolinate); 2-pyridinecarboxylic acid butyl ester; 6-ethyl-2-pyridinecarboxylic acid ethyl ester; 3,6-dichloro-2-pyridinecarboxylic acid methyl ester; 2-pyridineacetic acid methyl ester; 6-methyl-2-pyridineacetic acid methyl ester; 4-pyrimidine- carboxylic acid methyl ester; 5-methyl-2-pyrimidinecarboxylic acid methyl ester; 4-chloro-2-(methylthio)-5-pyrimidinecarboxylic acid ethyl ester; 4-pyridazinecarboxylic acid methyl ester; 3-hydroxy-4-quinolinecarboxylic acid methyl ester; 8-hydroxy-4-quinolinecarboxylic acid methyl ester; 4-hydroxy-7-(trifluoromethyl)-3-quinolinecarboxylic acid ethyl ester; 2-hydroxy-1,8-naphthyridine-3-carboxylic acid methyl ester; mixtures thereof and the like.

Particularly suitable nitrogen containing aromatic heterocyclic compounds having at least one acyclic carboxylic acid anhydride group which can be employed herein include, for example, pyrazinecarboxylic acid anhydride, 2-pyridinecarboxylic acid anhydride, 4-pyridinecarboxylic acid anhydride, 2-pyrazinecarboxylic acid anhydride with acetic acid; 2-pyrazinecarboxylic acid anhydride with propanoic acid; 2-pyridinecarboxylic acid anhydride with acetic acid; 2-pyridinecarboxylic acid anhydride with propanoic acid; pyrazinecarboxylic acid anhydride with methyl hydrogen carbonate; pyrazinecarboxylic acid anhydride with ethyl hydrogen carbonate; 2-pyridinecarboxylic acid anhydride with methyl hydrogen carbonate; 2-pyridinecarboxylic acid anhydride with ethyl hydrogen carbonate; mixtures thereof and the like.

Particularly suitable nitrogen containing aromatic heterocyclic compounds having at least one carboxylic acid halide group which can be employed herein include, for example, 2-pyrazinecarbonyl chloride; 2-pyridinecarbonyl chloride; 2-pyridinecarbonyl chloride hydrochloride; 3-pyridinecarbonyl chloride; 3-pyridinecarbonyl bromide; 4-pyridinecarbonyl chloride; 4-pyridinecarbonyl chloride hydrochloride; 2,3-pyridinedicarbonyl dichloride; 2,5-pyridinedicarbonyl dichloride; 2,6-pyridinedicarbonyl dichloride; 3,5-pyridinedicarbonyl dichloride; 4,6-pyridinedicarbonyl dichloride, mixtures thereof and the like.

Suitable fatty amines which can be employed herein include those having from about 4 to about 70, preferably from about 10 to about 24, carbon atoms such as, for example, N,N-dibutyl-1,3-propanediamine, N,N'-dipropyl-1,7-heptanediamine, N,N'-dioctyl-1,2-ethanediamine, N,N'-dioctyl-1,3-propanediamine, N,N-didecyl-1,3-propanediamine, 1,10-dodecanediamine, 1,12-dodecanediamine, 5,11-pentadecanediamine, 4,13-hexadecanediamine, 2,2,11-trimethyl-1,11-dodecanediamine, 5,13-diethyl-6,12-heptadecanediamine, 3,4-diethyl-4,13-hexadecanediamine, 12-ethyl-2-methyl-2-propyl-1,11-tetradecanediamine, 5,15-diethyl-5,14-nonadecanediamine, N-hexyl-1-hexanamine, N-octyl-1-octanamine, N-nonyl-1-nonanamine (Di-n-nonylamine), N-(2-aminoethyl)-1,2-ethanediamine, N-(3-aminopropyl)-1,4-butanediamine, N-(2-aminoethyl)-1,4-butanediamine, N-(3-aminopropyl)-1,3-propanediamine, bis-(2-aminopropyl) amine, 1-piperazineethanamine, 2-(3-aminopropylamino)ethanol, diethylenetriamine, triethylenetetramine, tetraethylenepentamine, pentaethylenehexamine, hexaethyleneheptamine, 3-isopropoxypropylamine, 3-(2-methoxyethoxy)propylamine, N-(3-ethoxypropyl)ethylamine, 4,4-diethoxybutylamine, 1-(2-aminoethylamino)-2-propanol, 6,9,12-trioxa-3,15-diazaheptadecane-1,17-diol, 3,6,9,12,15-pentaoxaheptadecane-1,17-diamine, N-(3-(decyloxy)-propyl)-1,3-propanediamine, 1-((2-aminoethyl)amino)-2-tetradecanol, 1-((3-aminopropyl)amino)-2-dodecanol, 5,5'-oxybis-1-pentanamine, 5-((3-ethylamino)propyl)amino-1-pentanol, 1-piperazinepropanol, cyclohexanebutylamine, cyclooctylamine, cyclododecylamine, N-methylcyclododecylamine, octamethyleneimine, 4-hexyloxyaniline, 4-pentyloxyaniline, 1,4-benzodioxan-6-amine, 2-amino-4-tert-butylphenol, 2-biphenylamine, 4-biphenylamine, 2-aminonaphthalene, 2-fluorenamine, 1-anthramine, 4-phenylbutylamine, 2-(benzyloxy)ethylamine, 2-($\beta$-phenethylamino)ethanethiol, 4-amino-1-benzylpiperidine, tall oil amine, soya amine, hydrogenated tallow amine, tallow amine, $C_8$–$C_{15}$ ether amine, ether-3-propylenediamines (Adogen ether amines), ether-1,2-ethylenediamines, N-alkyl-1,3-propylenediamines (Adogen fatty diamine), N-alkyl-1,2-ethylenediamines, partially alkoxylated or partially polyalkoxylated amines or polyamines, aminated polyoxyalkylene polyols, mixtures thereof and the like. Particularly suitable amines include 1-hexanamine(hexylamine), 1-heptanamine, 1-octanamine, 1-nonanamine, amine, 1-decanamine, 1-undecanamine, 1-dodecanamine (dodecylamine), 1-tridecanamine, 1-tetradecanamine, 1-pentadecanamine, 1-hexadecanamine, 1-heptadecanamine, 1-octadecanamine, N-methylhexanamine, N-methylheptanamine, N-methyl-1-decanamine, N-(1-methylethyl)-1-pentanamine, N-(1-methylethyl)-1-decanamine, N-methyl-1-octadecanamine, N-dodecyl-1-dodecanamine, N-decyl-1,2-ethanediamine, N-undecyl-1,2-ethanediamine, N-tridecyl-1,2-ethanediamine, N-pentadecyl-1,2-ethanediamine, N-hexadecyl-1,2-ethanediamine, N-heptadecyl-1,2-ethanediamine, N-octadecyl-1,2-ethanediamine, N-decyl-1,3-propanediamine, N-dodecyl-1,2-propanediamine, N-tetradecyl-1,3-propanediamine, N-hexadecyl-1,3-propane- diamine, N-heptadecyl-1,3-propanediamine, N-octadecyl-1,2-propanediamine, N-octadecyl-1,3-propanediamine, N-octadecyl-1,4-butanediamine, 9-octadecen-1-amine, 9,12-octadecadien-1-amine, 9,12,15-octadecatrien-1-amine, 9-eicosen-1-amine, 11-eicosen-1-amine, mixtures thereof and the like.

Thermal stability and film forming tenacity of a corrosion inhibitor is usually improved to some degree from crosslinking of the reactants. Polyamines can be mixed with monoamines to crosslink the reactants. Another necessary criteria for crosslinking the reactants is the presence of a nitrogen-containing aromatic heterocyclic compound having at least two carboxylic acid, acid chloride, ester, anhydride groups or mixtures of the groups.

In the case where the corrosion inhibitors of the present invention contain reactive amine hydrogens, they can be further reacted or neutralized with organic or mineral acids. The corrosion inhibitor of the present invention contains reactive amine hydrogens when the ratio of the

group of the aromatic heterocyclic material with at least one nitrogen atom to amine (—NH and —NH—) group of the organic amine is from about 0.10:1 to about 0.90:1. Such a case arises when an organic polyamine is reacted with an aromatic heterocyclic material with at least one nitrogen atom and one

group. The reactive amine hydrogens of the corrosion inhibitors of the present invention can be reacted or neutralized with an organic or mineral acid at a temperature from 25° to 300° C., the preferred temperature range with organic acid is from 150° to 230° C. These reactions can be carried out under reduced pressure if desired.

Suitable organic acids which can be employed herein include those represented by the following formulas

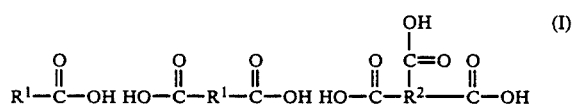

wherein $R^1$ is a hydrocarbyl group or a sulfur, halogen, nitro or hydroxyl substituted hydrocarbyl group having from about 1 to about 36 carbon atoms, preferably from about 1 to about 24 carbon atoms, most preferably an alkyl group having from about 1 to about 6 carbon atoms.

Suitable carboxylic acids which can be employed herein include, for example, heptanoic acid, octanoic acid, nonanoic acid, decanoic acid, undecanoic acid, dodecanoic acid (lauric acid), tridecanoic acid, tetradecanoic acid (myristic acid), pentadecanoic acid, hexadecanoic acid (palmitic acid), heptadecanoic acid, octadecanoic acid (stearic acid), nonadecanoic acid, eicosanoic acid, heneicosanoic acid, docosanoic acid, tricosanoic acid, tetracosanoic acid, tricontanoic acid, 2-propylpentanoic acid, 2-ethylhexanoic acid, 5-methyl-2-(5-methylhexyl)decanoic acid, 8-methylheptadecanoic acid, 3-methylpentadecanoic acid, 2-octenoic acid, trans-9-octadecenoic acid (elaidic acid), 12-octadecenoic acid, 9,12-octadecadienoic acid (linoleic acid), 13-docosenoic acid (erucic acid), 2,4-hexadienoic acid, 9,12,15-octadecatrienoic acid (linolenic acid), 5,8,11,14-eicosatetraenoic acid (arachidonic acid), 3,5-tetradecadienoic acid, 6-hexadecenoic acid, 3-hexyl-3-decenoic acid, 5,8-hexadecadienoic acid, 2-hydroxyl-1,2,3,-nonadecanetricarboxylic acid (agaricic acid), 11-bromoundecanoic acid, 2-bromohexadecanoic acid, 12-nitrododecanoic acid, 16-hydroxyhexadecanoic acid, 4-hydroxyoctadecanoic acid, 12-hydroxyoctadecanoic acid (DL-12-hydroxystearic acid), 4,4'-dithiobisbutanoic acid, decanedioic acid (sebacic acid), undecanedioic acid, dodecanedioic acid, tridecanedioic acid, tetradecanedioic acid, hexadecanedioic acid, trans-4-pentyl cyclohexanecarboxylic acid, cyclohexanebutanoic acid, cyclohexanehexanoic acid, 3-methyltricyclo(3.3.1.1$^{3.7}$)-decane-1-acetic acid, benzenebutanoic acid, benzenehexanoic acid, 11-phenoxyundecanoic acid, tall oil fatty acids, rosin acid, dimer acids such as Westvaco Diacid 1550, Empol 1010 dimer acid and Empol 1016 dimer acid, trimer acids such as Empol 1040 trimer acid, polycarboxylic acids such as Empol 1052 polybasic acid, mixtures thereof and the like. Particularly suitable organic acids include formic acid, acetic acid, propionic acid, butyric acid, hexanoic acid, acrylic acid, crotonic acid and the like. Hydrochloric acid, sulfuric acid, phosphoric acid and the like are suitable mineral acids.

If desired, the compositions of the present invention can be prepared in the presence of one or more solvents. Suitable such solvents include, for example, cyclic ethers, amides, furans, hydrocarbons, nitrogen-containing aromatic heterocycles, combinations thereof and the like. Particularly suitable solvents include, for example, tetrahydrofuran, dimethylformamide, dimethylacetamide, dioxane, benzene, toluene, pyridine, combinations thereof and the like.

The compositions of the present invention can be employed as a corrosion inhibitor as are conventional corrosion inhibitors. Generally, the product can be employed in corrosion inhibitor formulations as are known in the art. For example, the product can be dispersed or dissolved in a suitable carrier liquid or solvent such as water, alcohols, aromatic and aliphatic hydrocarbons, and the like, or mixtures thereof. Other additives include demulsifiers, water wetting agents, surfactants, viscosifiers, commingled gases, defoamers, other corrosion inhibitors such as polymeric materials and salts, organic and inorganic acids, iron control agents, sequestering and/or chelating agents, phosphates, quaternaries, amine salts, and the like. For example, surface active agents are used to assure complete dispersion of active ingredients throughout the corrosion inhibitor composition and thus provide a better contact of the corrosion inhibitor with the surface of the metal compound which is being protected. Some of the corrosion inhibitors of this invention form films on metal surfaces at least as readily as those known film forming corrosion inhibitors.

The corrosion inhibitor of this invention is employed in a functionally effective amount. That is, any quantity of corrosion inhibitor which will provide some degree of inhibition of corrosion is sufficient. Typical amounts of corrosion inhibitor which are employed in an oil and/or gas well treatment can range from about one to about 2,000 ppm for continuous treatment or about 200 to about 50,000 ppm for squeeze treatment, based on the weight of corrosive well fluids in contact with the metal compositions which are protected. Amounts of corrosion inhibitor in excess of 50,000 ppm can provide additional corrosion inhibition but at increased expense.

The corrosion inhibitors of this invention are highly stable to high temperatures and high pressures. Typically, corrosion inhibitors are employed in applications where temperatures range from about 100° F. (37.7° C.) to in excess of about 500° F. (260° C.), depending upon the composition of the inhibitor product. The corrosion inhibitors of this invention are especially useful at temperatures ranging from 300° F. (148.8° C.) to about 450° F. (232.2° C.).

The corrosion inhibitors of this invention inhibit corrosion to metal compositions used in down hole applications, preferably in excess of 80 percent corrosion protection. The corrosion inhibitors advantageously inhibit corrosion to metal compositions at elevated temperatures exceeding 250° F. in oil and gas well applications. Useful applications include oil and/or gas well drilling, completion, workover, stimulation, transfer, processing and storage applications.

The following examples are illustrative of the present invention.

CORROSION TESTING, 175° F. (79.4° C.)

Corrosion inhibition of various samples was determined under conditions which simulate conditions that exist in oil and 9as wells as follows. A brine solution containing 89.89 percent deionized water, 9.62 percent sodium chloride, 0.305 percent calcium chloride and a 0.186 percent hydrated magnesium chloride complex was prepared. This brine solution was saturated under carbon dioxide purge until a pH of 3.8 was achieved. The solution was treated with sodium persulfate to remove oxygen. The desired corrosion inhibitor was added to the solution. About 720 milliliters (ml) of this brine solution and 80 ml of kerosene (90% brine/-10% kerosene) treated with sodium persulfate were charged into a 32-ounce bottle. To this charge was added enough hydrated sodium sulfide to generate a suitable amount of hydrogen sulfide (i.e., about 300 ppm hydrogen sulfide based on total fluids).

Metal coupons (12″×¼″×1/16″, 304.8 mm×6.35 mm×1.59 mm) of 1020 carbon steel were degreased with an inhibited methylchloroform, acidized with 16 percent hydrochloric acid, washed and dried. Each coupon weighed about 19 g. A metal coupon was placed in the bottle containing the brine, kerosene and ingredients as previously described. The bottle was capped and acetic acid was injected into the bottle through a septum. The bottle was placed on a vertically rotating wheel held at 175° F. (79.4° C.) and the sample was rotated at 26 rpm for 24 hours (86400 s). The coupons were removed from the bottle, cleaned, washed, dried, reweighed and the percent protection afforded them by the inhibitor was calculated by the following formula:

$$\% \text{ protection} = 100 - \frac{\text{inhibitor coupon wt. loss}}{\text{blank coupon wt. loss}} \times 100$$

The weight loss was given to the nearest whole percent. The tests wherein no inhibitor was employed were for comparative purposes and are designated as blanks.

The corrosion rates were also determined in milliinches per year (mpy) by the following formula:

$$mpy = \frac{534 \text{ (mg Weight Loss of Coupon)}}{d \times a \times t}$$

$d$ = density of 1020 carbon steel = 7.86 g/ml
$a$ = surface area (in) of metal coupons
mg = milligrams
$t$ = test time in hours

CORROSION TESTING, 350° F. (177° C.)

The performance of 100 ppm of a corrosion inhibitor sample also was tested in a 350° F. (177° C.) wheel test containing 90 percent brine/8 percent heptane/2 percent kerosene at 2,000 psi pressure (25° C.) with 10 percent hydrogen sulfide, 10 percent carbon dioxide and 80 percent methane in a stainless steel pipe bomb. The sample was rotated at 26 rpm for 24 hours (86,400 s). Metal coupons (6″×¼″×1/16″, 152.4 mm×6.35 mm×1.59 mm) of 1020 carbon steel were degreased with chlorothene, scrubbed, washed with acetone and dried before being placed in the pipe bomb. After the test, the coupons were removed from the pipe bomb, scrubbed, washed with acetone and dried. Percent protection was calculated using the same equations as in the above 175° F. corrosion test.

EXAMPLE 1

Pyrazinecarboxylic acid (31.03 grams, 0.25 mole), tributylamine (44.6 grams, 0.24 mole) and dioxane (391.03 grams, 4.44 moles) were added to a one-liter resin kettle equipped with a thermometer, mechanical stirrer, condenser and addition funnel. The mixture was cooled to 6° C. with stirring via a sodium chloride-ice bath. Ethylchloroformate (27.15 grams, 0.25 mole) was added slowly via an addition funnel over 61 minutes (3660 s). Upon completion of the addition of ethylchloroformate, the mixture was warmed to 15° C. to allow dissolution of the solids, then cooled to 5° C. to give a chilled dioxane solution of pyrazinecarboxylic acid anhydride with ethyl hydrogen carbonate. KEMAMINE ®P-999 (69.88 grams, 0.25 mole) in dioxane (650 grams, 7.38 moles) was added slowly to the chilled dioxane solution of pyrazinecarboxylic acid anhydride with ethyl hydrogen carbonate over 330 minutes (19,800 s) at 5°-7° C. KEMAMINE ®P-999 is a mixture of $C_{16}$ to $C_{20}$ primary amines commercially available from Witco Chemical Corporation which consist primarily of 1-hexadecanamine, 1-octadecanamine, 9-octadecen-1-amine, 9,12-octadecadien-1-amine, 9,12,15-octadecatrien-1-amine and 9-eicosen-1-amine. The resultant yellow-orange reaction product was rotary evaporated under full vacuum at boiling water temperature to give a product of 92% mass yield.

The infrared spectrum of the product supported the presence of a secondary amide, methylene groups and free pyrazinecarboxylic acid. Multiple bands between 3000 $cm^{-1}$–3400 $cm^{-1}$ were assigned to the NH stretching vibration of a secondary amide. The bond at 1670 $cm^{-1}$ was assigned to the carbonyl stretching vibration (Amide I band) of a secondary amide. The band at 1530 $cm^{-1}$ was attributed to the N—H bending vibration (Amide II band) of a secondary amide. Absorption bands at 713 $cm^{-1}$, 1470 $cm^{-1}$, 2852 $cm^{-1}$ and 2925 $cm^{-1}$ supported the presence of methylene groups. The absorption band at 1725 $cm^{-1}$ was attributed to dimeric carboxylic carbonyl stretch.

The following pyrazineamides were identified by capillary gas chromatography-mass spectrometry.

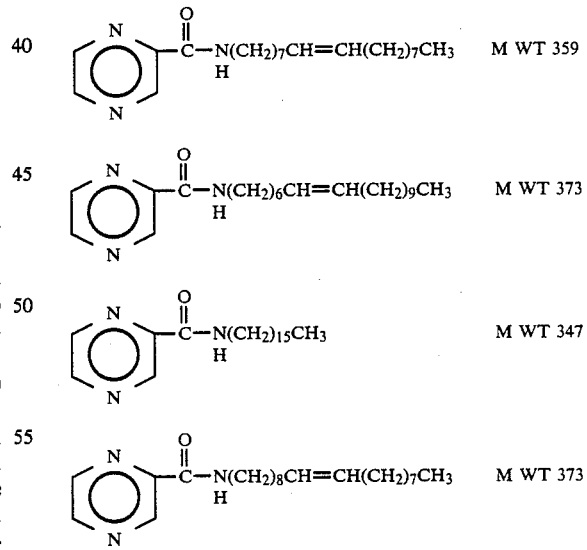

The carbon-carbon double bonds in the above structures could be located anywhere in the alkyl chains.

EXAMPLE 2

2-Pyridinecarboxylic acid (18.47 grams, 0.15 mole) and ADOGEN ®572 (40.13 grams, 0.12 mole) were charged to a 4-neck, 250 milliliter round bottom flask equipped with a mechanical stirrer, condenser, Barrett Trap, and temperature indicating device. The system was blanketed with nitrogen. ADOGEN®572 is primarily a mixture of octadecen-1-amine and octadecen-1,3-propanediamine commercially available from Sherex Chemical Co., Inc. The mixture was stirred and heated to 230° C. over a 37 minute (2220 s) period. A honey brown viscous liquid (48.89 grams) was recovered from the reactor and an aqueous solution of pyridine (5.48 grams) was recovered from the Barrett Trap.

Infrared spectroscopy supported the presence of a secondary amide, methylene groups and no free 2-pyridinecarboxylic acid. Multiple bands between 3000 cm$^{-1}$ 3440 cm$^{-1}$ were assigned to the NH stretching vibration of a secondary amide. The intense absorption band at 1675 cm$^{-1}$ was attributed to the carbonyl stretching vibration of a secondary amide. The band at 1530 cm$^{-1}$ was attributed to the N-H bending vibration of a secondary amide. The presence of methylene groups were supported by absorption bands at 722 cm$^{-1}$, 1470 cm$^{-1}$, 2855 cm$^{-1}$ and 2925 cm$^{-1}$.

Flame ionization capillary gas chromatography indicated 70% conversion to amide products based on area percent. Capillary gas chromatography mass spectrometry shows that the major constituents of the reaction product are

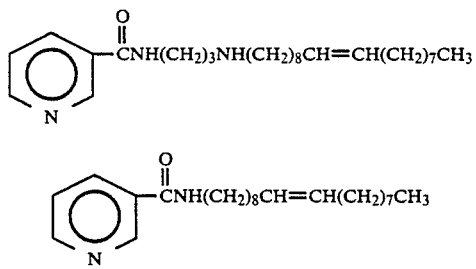

The carbon-carbon double bond in the above structures could be located anywhere in the alkyl chain.

EXAMPLE 3

2-Pyrazinecarboxylic acid (12.56 grams, 0.10 mole) and ADOGEN®572 (30.68 grams, 0.095 mole) were charged to a reactor of the type described in Example 2. The reactor contents were purged with nitrogen. The mixture was stirred and heated gradually to 230° C. over a 130 minute (7800 s) interval and maintained at 230° C. for an additional 105 minutes (6300 s). A dark red brown viscous liquid (37.32 grams) was recovered from the reactor and an aqueous solution of pyrazine (3.65 grams) was collected from the Barrett Trap.

The infrared spectrum of dark red brown viscous liquid resembled the spectrum of the honey brown viscous liquid of Example 2. Flame ionization capillary gas chromatography indicated that 80% of the initial fatty amines were converted to amide products containing the pyrazine nucleus.

EXAMPLE 4

2-Pyrazinecarboxylic acid (12.56 grams, 0.10 mole) and KEMAMINE® P-650 (21.56 grams) were added to a reactor of the type described in Example 2. KEMAMINE® P-650 is a mixture of $C_{11-18}$ primary amines commercially available from Witco Chemical Corp. which consists primarily of a mixture of 1-decanamine, 1-dodecanamine, 1-tetradecanamine, 1-hexadecanamine, 1-octadecanamine, and octadecen-1-amine. The reactor contents were purged with nitrogen. The mixture was stirred and heated gradually over 125 minutes (7500 s) to 230° C. The reactor contents were sampled at 150° and 200° C. 31.55 grams of reaction product and 1.06 grams of overhead liquid were recovered. Flame ionization capillary gas chromatography indicated the typical formation of the amide reaction product.

EXAMPLE 5

2-Ethylpicolinate (24.70 grams, 0.16 mole) and ADOGEN®572 (52.86 grams, 0.16 mole) were weighed into a reactor of the type described in Example 2. The reactor contents were blanketed with nitrogen. The mixture was then heated to 230° C. over a 65 minute (3900 s) period until no more condensate flowed into the Barrett Trap. The yellow contents (69.20 grams) in the reactor were cooled to room temperature. 6.59 grams of overhead liquids were recovered from the Barrett Trap.

Capillary gas chromatography indicated that about 90% of the initial ADOGEN® 572 was converted to amide products.

EXAMPLE 6

4-Pyridinecarbonyl chloride hydrochloride (53.6 grams, 0.3 mole) was weighed into a reactor of the type described in Example 2. KEMAMINE® P-650 (65.8 grams, 0.3 mole) was added to the 4-pyridinecarbonyl chloride hydrochloride with an addition funnel over a 75 minute (4500 s) period. Then dioxane (50 milliliters) was added to the reactor contents. Dioxane and water were removed with a Barrett trap as the reaction temperature was incrementally increased to 235° C. over an 85 minute (5100 s) period. A soft brown solid (105.56 grams) was recovered from the reactor. The brown solid was dissolved in water for the corrosion inhibition tests.

EXAMPLE 7

The soft brown solid (30.08 grams) from Example 6 was added to a 1-liter beaker. Sodium hydroxide (12.28 grams, 0.31 mole) and water (65.27 grams, 3.62 moles) were added to the beaker. The contents of the beaker were stirred at boiling water temperature for 10 minutes (600 s). A brownish solid precipitated from the solution at room temperature. The brown solid was extracted with chloroform (500 milliliters). The chloroform was removed by rotary evaporation under full vacuum. Isopropanol was added to the solid and removed by rotary evaporation under full vacuum to give a fatty light tan solid (28.11 grams). The light tan solid was dissolved in water for the corrosion inhibition tests.

EXAMPLE 8

2-Pyridinecarboxylic acid (24.67 grams, 0.2 mole), 2,5-pyridinedicarboxylic acid (17.09 grams, 0.16 mole), Witco Kemamine P-650 mixed amines (42.96 grams, 0.2 mole), and triethylenetetramine (14.76 grams, 0.1 mole) were added to a reactor of the type described in Example 2. The mixture was heated gradually to 250° C. over a 500 minute (30,000 s) period until condensate ceased to flow into the Barrett trap. A brown solid product (85.12 grams) was recovered from the reactor and clear overhead liquids (13.19 grams) were recovered from the Barrett trap. The brown solid was dissolved in a mixture of ethanol and xylene for the corrosion inhibition tests.

EXAMPLE 9

2-Pyridinecarboxylic acid (48.08 grams, 0.34 mole) was weighed into a reactor of the type described in Example 2. Anhydrous isopropanol was added to the 2-pyridinecarboxylic acid to form a stirrable slurry. Triethylenetetramine (33.32 grams, 0.23 mole) was added to the reactor contents by using an addition funnel at 83° C. over a 152 minute (9120 s) period. Isopropanol and water were removed by using a Barrett trap. The temperature was increased to a maximum of 235° C. over a 110 minute (6600 s) period. A light beige viscous liquid (64.2 grams) was recovered from the reactor. This liquid was subjected to simple distillation at a head temperature of 190° C. and 3.5 mm mercury vacuum giving a light golden brown viscous liquid (44.94 grams). Capillary gas chromatography of the light golden brown liquid indicated the absence of unreacted triethylenetetramine or 2-pyridinecarboxylic acid. The light golden brown liquid was dissolved in isopropanol for the corrosion inhibition tests.

EXAMPLE 10

The light golden brown viscous liquid (10.57 grams, 0.04 mole) from Example 9 was weighed into a reactor of the type described in Example 2. Anhydrous isopropanol (16.17 grams) was added to the reactor contents to facilitate stirring. Then 37% hydrochloric acid (16.67 grams, 0.17 mole) was added dropwise by using an addition funnel. The reactants were heated to 80° C. for 30 minutes (1800 s). Isopropanol and water were removed by using a Barrett trap. The reaction product was heated under a vacuum of 3.5 mm mercury for an additional 15 minutes (900 s) at 90° C. The final product was a light pink taffy-like solid (16.51 grams). The light pink solid was dissolved in isopropanol for the corrosion inhibition tests.

EXAMPLE 11

The light golden brown viscous liquid (10.09 grams, 0.04 mole) from Example 9 was weighed into a reactor of the type described in Example 2. Glacial Acetic Acid was added dropwise to the reactor contents over a five minute (300 s) period by using an addition funnel. The reactor contents were heated to 125° C. for 15 minutes (900 s) giving a yellow brown viscous liquid (19.82 grams). The yellow brown liquid was dissolved in isopropanol for the corrosion inhibition tests.

EXAMPLE 12

The yellow brown viscous liquid from Example 11 was added to a reactor of the type described in Example 2. The reactor contents were heated to 235° C. over a period of 120 minutes (7200 s) giving a dark brown solid. The dark brown solid was dissolved in isopropanol for the corrosion inhibition tests.

EXAMPLE 13

2-Pyridinecarboxylic acid (12.82 grams, 0.1 mole) was weighed into a reactor of the type described in Example 2. Isopropanol (110 milliliters) was added to the 2-pyridinecarboxylic acid to form a slurry. The slurry was heated to 83° C. under a nitrogen atmosphere and a solution of tetraethylenepentamine (29.62 grams, 0.15 mole) in isopropanol (50 milliliters) was added dropwise from an addition funnel during a 55 minute (3300 s) period. As the temperature was increased incrementally to 235° C., isopropanol and water were removed with a Barrett trap. A light yellow viscous liquid (38.99 grams) was recovered from the reactor. This liquid was subjected to simple distillation at a head temperature of 180° C. and 3.5 mm mercury vacuum giving a light yellow viscous liquid (26.89 grams). The light yellow viscous liquid was dissolved in isopropanol for the corrosion inhibition tests.

The above prepared materials were tested for corrosion inhibition at 80° C. and 177° C. The results for the 80° C. tests are given in Table I and the 177° C. results are given in Table II.

TABLE I

| Test | Inhibitor From | Inhibitor Concentration (ppm[1]) | Weight Loss (gms) | Corrosion Rate MPY[2] (mmpY[3]) | % Protection |
|---|---|---|---|---|---|
| 1 | None | 0 | 0.2046 | 79.7 (2.024) | 0 |
|  | Ex. 1 | 100 | 0.0105 | 4.1 (0.104) | 94.9 |
| 2 | None | 0 | 0.3328 | 131.0 (3.327) | 0 |
|  | CORBAN A-163 | 100 | 0.0658 | 26.0 (0.660) | 80.2 |
| 3 | None (Blank) | 0 | 0.1798 | 67.4 (1.712) | 0 |
|  | Ex. 2 | 5 | 0.0247 | 9.3 (0.236) | 86.3 |
| 4 | None | 0 | 0.1558 | 58.6 (1.482) | 0 |
|  | Ex. 2 | 100 | 0.0095 | 3.6 (0.091) | 93.9 |
| 5 | None | 0 | 0.1773 | 66.5 (1.689) | 0 |
|  | Ex. 3 | 1 | 0.0331 | 12.3 (0.312) | 81.3 |
| 6 | None | 0 | 0.1798 | 67.4 (1.712) | 0 |
|  | Ex. 3 | 5 | 0.0110 | 4.1 (0.104) | 93.9 |
| 7 | None | 0 | 0.1014 | 37.7 (0.958) | 0 |
|  | Ex. 3 | 10 | 0.0066 | 2.5 (0.064) | 93.4 |
| 8 | None | 0 | 0.1558 | 58.6 (1.488) | 0 |
|  | Ex. 3 | 100 | 0.0071 | 2.7 (0.069) | 95.4 |
| 9 | None | 0 | 0.2380 | 90.6 (2.301) | 0 |
|  | Ex. 4 (150° C. Sample) | 100 | 0.0849 | 32.1 (0.815) | 64.3 |
| 10 | None | 0 | 0.2294 | 87.2 (2.215) | 0 |
|  | Ex. 4 (200° C. Sample) | 100 | 0.0099 | 3.7 (0.094) | 95.7 |
|  | Ex. 4 (230° C. Sample) | 100 | 0.0058 | 2.2 (0.056) | 97.5 |
| 11 | None | 0 | 0.1834 | 70.4 (1.788) | 0 |
|  | Ex. 5 | 100 | 0.0141 | 5.4 (0.137) | 92.3 |
| 12 | None | 0 | 0.1774 | 67.2 (1.707) | 0 |
|  | Ex. 6 | 100 | 0.0063 | 2.4 (0.061) | 96.4 |
|  | Ex. 7 | 100 | 0.0099 | 3.7 (0.094) | 94.4 |
|  | Ex. 9 | 100 | 0.0566 | 21.4 (0.544) | 68.1 |
|  | Ex. 13 | 100 | 0.0823 | 30.8 (0.782) | 53.6 |
| 13 | None | 0 | 0.2024 | 77.1 (1.958) | 0 |
|  | Ex. 8 | 100 | 0.0141 | 5.4 | 93.0 |

TABLE I-continued

80° C. WHEEL TEST

| Test | Inhibitor From | Inhibitor Concentration (ppm[1]) | Weight Loss (gms) | Corrosion Rate MPY[2] (mmpY[3]) | % Protection |
|---|---|---|---|---|---|
| 14 | None | 0 | 0.1800 | 67.5 (0.137) (1.715) | 0 |
|  | Ex. 10 | 100 | 0.0745 | 28.6 (0.726) | 58.6 |
|  | Ex. 11 | 100 | 0.0549 | 20.6 (0.523) | 69.5 |
| 15 | None | 0 | 0.1975 | 75.6 (1.920) | 0 |
|  | Ex. 12 | 100 | 0.0200 | 7.7 (0.196) | 89.9 |

[1] ppm = parts per million by weight
[2] MPY = mils per year
[3] mmPY = millimeters per year The data in Table I demonstrates that 100 ppm inhibitor of this invention exhibits good corrosion protection under simulated down hole tests at 80° C. In most cases, corrosion protection is much better than that exhibited by commercially available Corban A-163. Therefore, the corrosion inhibitor of this invention is suitable for the protection of metal alloys against corrosion due to coercive fluids produced in oil and gas well formations and harmful to said metal alloys at or below 80° C. In addition, the corrosion inhibitors of this invention are suitable for the corrosion protection of pipelines, storage tanks, pumps, etc., that exist for the purpose of separating, and/or recovering gas from the produced fluids.

TABLE II

177° C. WHEEL TEST

| Test No. | Inhibitor From | Inhibitor Conc. (ppm[3]) | Weight Loss (gms) | % Protection |
|---|---|---|---|---|
| 1 | None | 0 | 0.1437 | 0 |
|  | Example 1 | 100 | 0.0317 | 78 |
| 2 | None | 0 | 0.1197 | 0 |
|  | Example 2 | 100 | 0.0238 | 77.4 |
|  | Example 3 | 100 | 0.0059 | 95.1 |
| 3 | None | 0 | 0.1022 | 0 |
|  | Example 5 | 100 | 0.0149 | 86 |
| 4 | None | 0 | 0.1082 | 0 |
|  | C-4[1] | 100 | 0.0246 | 77 |
|  | C-5[2] | 100 | 0.0485 | 55 |

[1] C-4 is a commercial corrosion inhibitor available from Dowell-Schlumberger as Corban A-163.
[2] C-5 is a commercial corrosion inhibitor available from Henkel as Textamine T5D.
[3] ppm = parts per million parts by weight.

The above data shows that the inhibitors of this invention advantageously provide good corrosion protection at 177° C. (350° F.) demonstrating the value of these inhibitors for high temperature and high pressure oil and gas well down hole environments. The corrosion inhibitor protection is equivalent to or better than the values obtained for commercially available corrosion inhibitors (Sample Nos. C-4 and C-5).

What is claimed is:

1. A method for preventing the corrosion of a metal composition in contact with a down hole well fluid, which method comprises contacting the surface of said metal composition with an effective amount of, as a corrosion inhibitor, a composition which comprises the reaction product of the components selected from the group consisting of (A) at least one pyrazine, pyrimidine, pyridazine, quinoline, isoquinoline, cinnoline, naphthyridine, or pyridine compound, which compound(s) is (are) free of unsaturated hydrocarbon substituents, having one or more rings, at least one nitrogen atom and containing at least one group selected from
(1) carboxylic acid,
(2) carboxylic acid ester,
(3) acyclic carboxylic acid anhydride,
(4) carboxylic acid halide or
(5) combination thereof; with (B) an organic amine having from about 1 to about 72 carbon atoms; and (C) optionally reacted or neutralized with a mineral acid or an organic acid having from about 1 to about 36 carbon atoms; and wherein components (A) and (B) are present in quantities which provide a ratio of —CO— groups to —NH$_2$ and/or —NH— groups of from about 0.1:1 to about 1.2:1 and component (C) is present in a quantity which provides a ratio of mineral acid or carboxylic acid to reactive amine hydrogen of the product formed from the reaction of components (A) and (B) of from about zero:1 to about 2:1.

2. A method of claim 1 wherein component (A) is substituted pyrazine, pyridine, quinoline, isoquinoline or quinoxaline or combination of such substituted materials; component (B) is a material represented by the formulas $$H_2N(CH_2)_pCH_3,$$

$$H_2N(CH_2)_p(CH=CH)_nCH_3,$$

$$H_2N((CH_2)_m-NH)_m(CH_2)_m-NH_2,$$

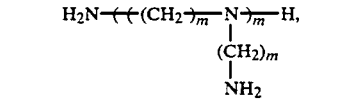

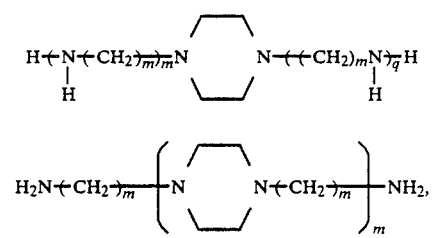

$$H_2N(CH_2)_m-NH(CH_2)_pCH_3, \text{ or}$$

$$H_2N(CH_2)_m-NH(CH_2)_p(CH=CH)_nCH_3, \text{ or}$$

wherein m has a value from 1 to about 10, n has a value from 1 to about 5, p has a value from 7 to about 72, q has a value from zero to about 10; and wherein the carbon-carbon double bond (—CH=CH)— is located anywhere through the saturated hydrocarbon chain ((—CH$_2$)$_p$); component (C) is an organic carboxylic acid having from 1 to about 6 carbon atoms; components (A) and (B) are present in quantities which provide a ratio of —CO— groups to —NH$_2$ and/or —NH— groups of from about 0.75:1 to about 1.2:1 and component (C) is present in a quantity which provides a ratio of mineral acid or carboxylic acid to reactive amine hydrogen of the product formed from the reaction of components (A) and (B) of from about 0.75:1 to about 1.5:1.

3. A method of claim 2 wherein component (A) is 2-pyridinecarboxylic acid; 2-pyridinecarboxylic acid ethyl ester; 2-pyridinecarboxylic acid anhydride with ethyl hydrogen carbonate; 4-pyridinecarbonyl chloride hydrochloride, pyrazinecarboxylic acid, pyrazinecarboxylic acid methyl ester, pyrazinecarboxylic acid anhydride with ethyl hydrogen carbonate, pyrazinecarbonyl chloride or a combination thereof; component (B) is 1-decanamine, 1-undecanamine, 1-dodecanamine, 1-tridecanamine, 1-tetradecanamine, 1-pentadecanamine, 1-hexadecanamine, 1-heptadecanamine, 1-octadecanamine, 9-octadecen-1-amine, 9,12-octadecadien-1-amine, 9,12,15-octadecatrien-1-amine, 9-eicosen-1-amine, octadecen-1,3-propanediamine or a combination thereof; component (C) is acetic acid; components (A) and (B) are present in quantities which provide a ratio of —CO— groups to —NH$_2$ and/or —NH— groups of from about 0.9:1 to about 1.1:1 and component (C) is present in a quantity which provides a ratio of acetic acid to reactive amine hydrogen of the product formed from the reaction of components (A) and (B) of from about 0.9:1 to about 1.1:1.

4. A method of claim 1 wherein the corrosion inhibitor composition is employed in an amount of from about one to about 2,000 parts per million parts by weight of the well fluid which is in contact with the metal composition.

5. A method of claim 4 wherein the corrosion inhibitor is contacted with a carrier liquid and contacted with the well fluid.

6. A method of claim 2 wherein the corrosion inhibitor composition is employed in an amount of from about one to about 2,000 parts per million parts by weight of the well fluid which is in contact with the metal composition.

7. A method of claim 6 wherein the corrosion inhibitor is contacted with a carrier liquid and contacted with the well fluid.

8. A method of claim 3 wherein the corrosion inhibitor composition is employed in an amount of from about one to about 2,000 parts per million parts by weight of the well fluid which is in contact with the metal composition.

9. A method of claim 8 wherein the corrosion inhibitor is contacted with a carrier liquid and contacted with the well fluid.

* * * * *